US00PP29950P2

(12) United States Plant Patent
Noordhuis et al.

(10) Patent No.: US PP29,950 P2
(45) Date of Patent: Dec. 4, 2018

(54) ***CAREX* PLANT NAMED 'ET CRX02'**

(50) Latin Name: *Carex hybrida*
Varietal Denomination: ET CRX02

(71) Applicants: Bart Noordhuis, Boijl (NL); Elisabeth Bisschop, Boijl (NL)

(72) Inventors: Bart Noordhuis, Boijl (NL); Elisabeth Bisschop, Boijl (NL)

(73) Assignee: Eternal Plant Boijl B.V., Boijl (NL)

( * ) Notice: Subject to any disclaimer, the term of this patent is extended or adjusted under 35 U.S.C. 154(b) by 0 days.

(21) Appl. No.: 15/731,451

(22) Filed: Jun. 12, 2017

(51) Int. Cl.
*A01H 5/12* (2018.01)

(52) U.S. Cl.
USPC ..... Plt./384

(58) Field of Classification Search
USPC ..... Plt./384
See application file for complete search history.

(56) References Cited

FOREIGN PATENT DOCUMENTS

QZ PBR 20162001 12/2016

OTHER PUBLICATIONS

UPOV hit on Plant Breeder's Right for a *Carex* named 'ET CRX02', QZ PBR 20162001, published Dec. 15, 2016.*

* cited by examiner

*Primary Examiner* — Anne Marie Grunberg
(74) *Attorney, Agent, or Firm* — C. A. Whealy

(57) ABSTRACT

A new and distinct cultivar of *Carex* plant named 'ET CRX02', characterized by its relatively compact and broad outwardly arching plant habit; moderately vigorous to vigorous growth habit; long lanceolate solid green-colored leaves; and good postproduction longevity and garden performance.

2 Drawing Sheets

Botanical designation: *Carex hybrida.*
Cultivar denomination: 'ET CRX02'.

BACKGROUND OF THE INVENTION

The present invention relates to a new and distinct *Carex* plant, botanically known as *Carex hybrida* and hereinafter referred to by the name 'ET CRX02'.

The new *Carex* plant is a product of a planned breeding program conducted by the Inventors in Boijl, The Netherlands. The objective of the breeding program was to create new compact *Carex* plants with an elegant plant habit.

The new *Carex* plant originated from a cross-pollination conducted by the Inventors in Boijl, The Netherlands in 2010 of a proprietary selection of *Carex hybrida* identified as code number 520, as the female, or seed, parent, not patented, with a proprietary selection of *Carex hybrida* identified as code number 6-90, as the male, or pollen, parent, not patented. The new *Carex* plant was discovered and selected by the Inventors as a single plant from within the progeny of the stated cross-pollination grown in a controlled greenhouse environment in Boijl, The Netherlands in early 2011.

Asexual reproduction of the new *Carex* plant by divisions in a controlled greenhouse environment in Boijl, The Netherlands since early 2011 has shown that the unique features of this new *Carex* plant are stable and reproduced true to type in successive generations.

SUMMARY OF THE INVENTION

Plants of the new *Carex* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ET CRX02'. These characteristics in combination distinguish 'ET CRX02' as a new and distinct *Carex* plant:

1. Relatively compact and broad outwardly arching plant habit.
2. Moderately vigorous to vigorous growth habit.
3. Long lanceolate solid green-colored leaves.
4. Good postproduction longevity and garden performance.

Plants of the new *Carex* differ primarily from plants of the female parent selection in the following characteristics:

1. Leaves of plants of the new *Carex* are longer than leaves of plants of the female parent selection.
2. Leaves of plants of the new *Carex* are lighter green in color than leaves of plants of the female parent selection.
3. Peduncles of plants of the new *Carex* are shorter than peduncles of plants of the female parent selection.

Plants of the new *Carex* differ primarily from plants of the male parent selection in the following characteristics:

1. Plants of the new *Carex* are more compact than plants of the male parent selection.
2. Leaves of plants of the new *Carex* are shorter than leaves of plants of the male parent selection.

Plants of the new *Carex* can be compared to plants of the *Carex hybrida* 'ET CRX01', disclosed in U.S. Plant Pat. No. 26,199. In side-by-side comparisons, plants of the new

*Carex* differ primarily from plants of 'ET CRX01' in leaf color as plants of 'ET CRX01' have variegated leaves with green-colored centers and white-colored margins. Additionally, plants of the new *Carex* are more compact and have shorter leaves than plants of 'ET CRX01'.

BRIEF DESCRIPTION OF THE PHOTOGRAPHS

The accompanying photographs illustrate the overall appearance of the new *Carex* plant showing the colors as true as it is reasonably possible to obtain in colored reproductions of this type. Colors in the photographs may differ slightly from the color values cited in the detailed botanical description which accurately describe the colors of the new *Carex* plant.

The photograph on the first sheet is a side perspective view of a typical plant of 'ET CRX02' grown in a container.

The photograph on the second sheet is a close-up view of a typical plant of 'ET CRX02'.

DETAILED BOTANICAL DESCRIPTION

The aforementioned photographs and following observations and measurements describe plants grown during the spring in 26-cm containers in an outdoor nursery in Boijl, The Netherlands and under cultural practices typical of commercial *Carex* plant production. During the production of the plants, day temperatures ranged from 18° C. to 32° C. and night temperatures ranged from 6° C. to 20° C. Plants were one year old when the photographs and botanical description were taken. In the following description, color references are made to The Royal Horticultural Society Colour Chart, 2001 Edition, except where general terms of ordinary dictionary significance are used.

Botanical classification: *Carex hybrida* 'ET CRX02'.

Parentage:

*Female, or seed, parent*.—Proprietary selection of *Carex hybrida* identified as code number 520, not patented.

*Male, or pollen, parent*.—Proprietary selection of *Carex hybrida* identified as code number 6-90, not patented.

Propagation:

*Type*.—By divisions.

*Time to initiate roots, summer and winter*.—About six weeks at temperatures about 20° C.

*Time to produce a rooted young plant, summer and winter*.—About three months at temperatures about 20° C.

*Root description*.—Medium in thickness, fleshy; color, close to 162D.

*Rooting habit*.—Freely branching habit; medium density.

Plant description:

*Plant and growth habit*.—Relatively compact and broad outwardly arching plant habit; about 30 main shoots (culms) develop from the base; moderately vigorous to vigorous growth habit; moderate to fast growth rate.

*Plant height, soil level to top of foliar plane*.—About 25 cm.

*Plant diameter or spread*.—About 60 cm.

Leaf description:

*Arrangement*.—Alternate; sessile.

*Length*.—About 30 cm to 40 cm.

*Width*.—About 1.2 cm.

*Shape*.—Lanceolate; strongly curved and arching.

*Apex*.—Long acuminate to long aristate.

*Margin*.—Very finely serrate, sharp to the touch.

*Base*.—Sheathing; length of leaf sheath, about 3.6 cm.

*Texture and luster, upper surface*.—Smooth, glabrous; glossy.

*Texture and luster, lower surface*.—Smooth, glabrous; moderately glossy.

*Venation pattern*.—Parallel.

*Color*.—Developing leaves, upper surface: Close to 137A. Developing leaves, lower surface: Close to 144A. Fully expanded leaves, upper surface: Close to 139A; venation, close to 139B. Fully expanded leaves, lower surface: Close to 137C; venation, close to 137A.

Flower description:

*Flower type and arrangement*.—Terminal racemes with staminate and pistillate flowers arranged on spikelets; inflorescences upright and held above and beyond the foliar plane on strong peduncles.

*Inflorescence height*.—About 5 cm to 8 cm.

*Inflorescence width*.—About 1 cm to 2 cm.

*Flowering habit*.—Freely flowering with about 60 inflorescences developing per plant with about three to four flowers per spikelet.

*Flowering time*.—Plants begin flowering about eight to nine months after planting; plants flower continuously from late winter until late spring in The Netherlands.

*Fragrance*.—None detected.

*Flower buds*.—Length, staminate and pistillate flowers: About 3 cm to 4 cm. Diameter, staminate and pistillate flowers: About 3 mm. Shape, staminate and pistillate flowers: Lanceolate. Color, staminate flowers: Close to N199C. Color, pistillate flowers: Close to 144A and 145A.

*Spikelets*.—Diameter: About 1.5 cm. Depth: About 3 cm to 4 cm. Shape: Sedge-like, narrowly ovate. Persistence of spikelets: Persistent. Staminate flowers: Typically with one lemma and one glume. Lemma and glume: Length: About 5 mm to 6 mm. Width: About 0.5 mm. Shape: Lanceolate. Apex: Long and narrowly acute. Margin: Entire. Texture and luster, upper and lower surfaces: Smooth, glabrous; dull. Color, upper and lower surfaces: Close to 11C to 11D. Pistillate flowers: Typically with one lemma and no glume. Lemma: Length: About 5 mm. Width: About 1 mm. Shape: Lanceolate. Apex: Long and narrowly acute. Margin: Entire. Texture and luster, upper and lower surfaces: Smooth, glabrous; dull. Color, upper and lower surfaces: Close to 145D; towards the apex, close to 11C to 11D.

*Peduncles*.—Length: About 15 cm to 18 cm. Diameter: About 3 mm to 5 mm. Aspect: About 20° from vertical, arching outwardly with development. Strength: Strong. Texture and luster: Smooth, glabrous; dull. Color: Close to 137B.

*Reproductive organs*.—Stamens: Quantity per flower: Numerous. Anther length: About 4 mm. Anther shape: Oval. Anther color: Close to 11D. Pollen amount: Abundant. Pollen color: Close to 11C. Pistils: Quantity per flower: One. Pistil length: About 1 mm to 2 mm. Style length: About 1 mm. Style color:

Close to 145A to 145B. Stigma shape: Fimbriate. Stigma color: Close to N199B to N199C. Ovary color: Close to 145A.

*Fruits and seeds*.—Fruit and seed production has not been observed on plants of the new *Carex* to date.

Disease & pest resistance: Plants of the new *Carex* have not been shown to be resistant to pathogens and pests common to *Carex* plants to date.

Postproduction longevity: Good postproduction longevity, plants of the new *Carex* are durable and maintain good leaf substance for about three months.

Garden performance: Plants of the new *Carex* have been observed to have good garden performance and to tolerate wind, rain and temperatures ranging from about −20° C. to about 35° C.

It is claimed:

1. A new and distinct *Carex* plant named 'ET CRX02' as illustrated and described.

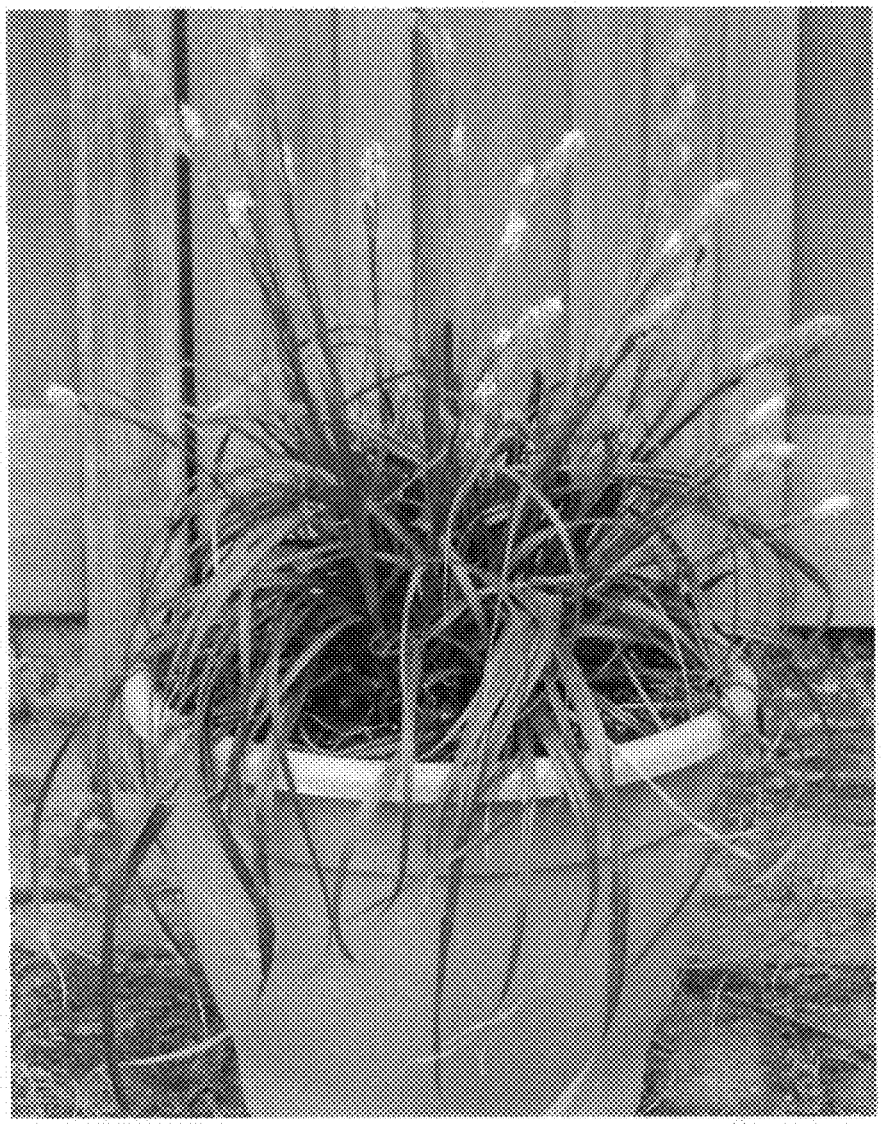

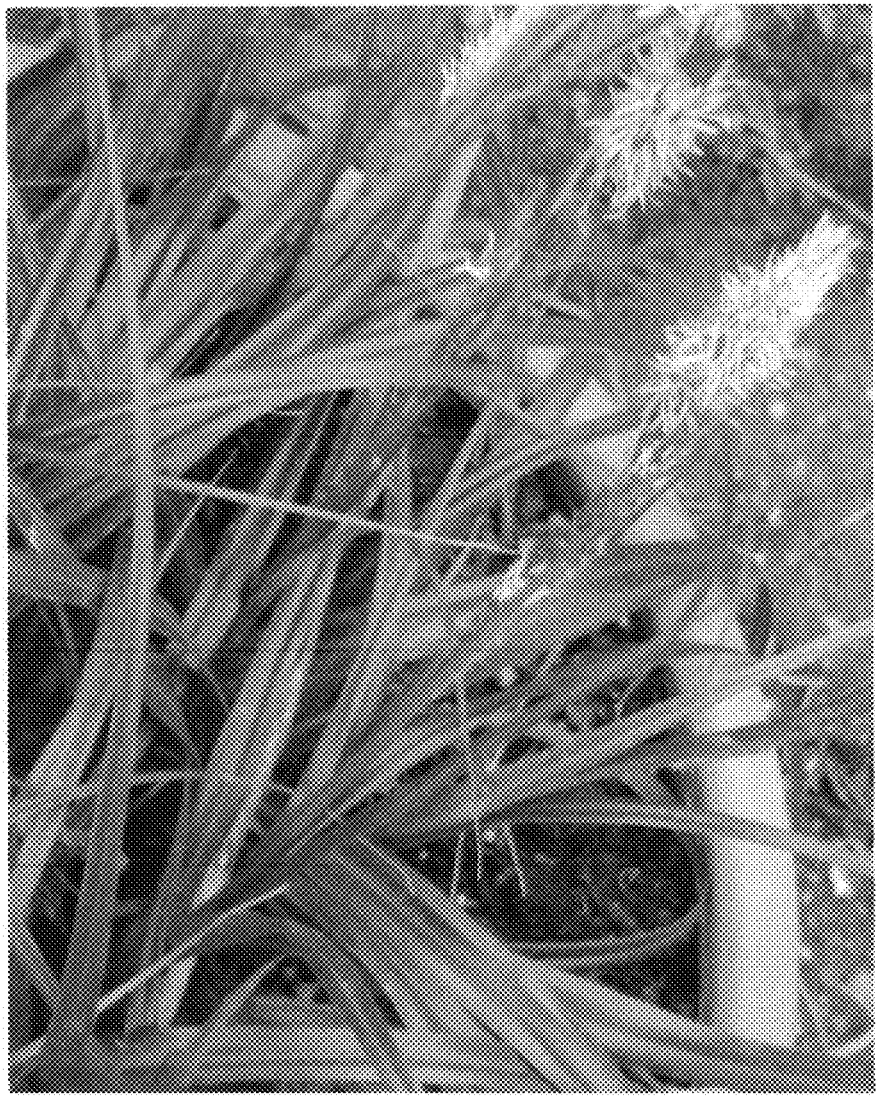

* * * * *